United States Patent [19]

Narisada et al.

[11] 4,201,782
[45] May 6, 1980

[54] THIADIAZOLYL CEPHALOSPORIN ANALOGS

[75] Inventors: Masayuki Narisada, Ibaraki; Wataru Nagata, Nishinomiya, both of Japan

[73] Assignee: Shionogi & Co., Ltd., Osaka, Japan

[21] Appl. No.: 936,506

[22] Filed: Aug. 24, 1978

[30] Foreign Application Priority Data

Aug. 25, 1977 [JP] Japan .................................. 52/102261

[51] Int. Cl.² ................ A61K 31/41; C07D 413/02; C07D 413/14
[52] U.S. Cl. ............................... 424/248.51; 544/90; 549/79; 560/76
[58] Field of Search ............................... 544/21, 29, 90; 424/248.51

[56] References Cited

U.S. PATENT DOCUMENTS

| 4,031,083 | 6/1977 | Haviv et al. ................ 544/21 X |
| 4,045,438 | 8/1977 | Haviv et al. ................ 544/21 X |

FOREIGN PATENT DOCUMENTS 52-65292  5/1977  Japan ........................................ 544/90

OTHER PUBLICATIONS

Lednicer et al., The Organic Chemistry of Drug Synthesis, frontispage & 416–422, John Wiley and Sons, NY (1977).

Firestone et al., J. Med. Chem. vol. 20, pp. 551–556 (4/77).

Primary Examiner—John D. Randolph
Attorney, Agent, or Firm—Wenderoth, Lind & Ponack

[57] ABSTRACT

Antibacterial 7β-arylmalonamido-7α-methoxy-3-optionally alkylated thiadiazolylthiomethyl-1-oxadothiacephalosporins of the following formula:

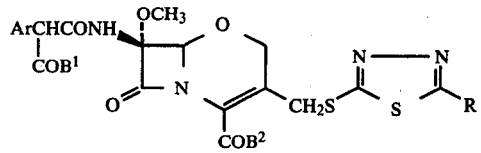

(wherein
Ar is 2-thienyl, 3-thienyl, phenyl, p-hydroxyphenyl, p-acyloxyphenyl or p-protected hydroxyphenyl;
$COB^1$ and $COB^2$ each is carboxy, protected carboxy or a carboxylate salt; and
R is hydrogen or lower alkyl), processes for preparing said compounds, a pharmaceutical or veterinary composition comprising the said compounds and pharmaceutical carrier and a method for treating or preventing human or veterinary infectious diseases comprising administering the said compound.

62 Claims, No Drawings

THIADIAZOLYL CEPHALOSPORIN ANALOGS

COMPOUNDS INVENTED

This invention relates to 7β-arylmalonamido-7α-methoxy-3-(optionally alkylated thiadiazolylthio)-1-oxadethiacephalosporins (I) of the following formula:

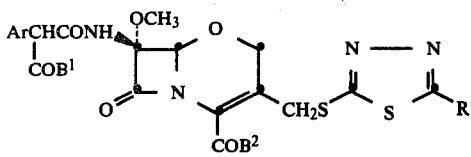

(wherein
Ar is phenyl, p-hydroxyphenyl, p-acyloxyphenyl, p-protected hydroxyphenyl, 2-thienyl or 3-thienyl;
COB¹ and COB² each is carboxy, protected carboxy or a carboxylate salt; and
R is hydrogen or lower alkyl).

BACKGROUND OF THE INVENTION

Cephalosporin analogs having an oxygen atom in place of the sulfur atom in the nucleus have been described in the Journal of Heterocyclic Chemistry, Volume 5, page 779 (1968) by J. C. Sheehan and M. Dadic; German Patent Application (OLS) No. 2,219,601 (1972); Canadian Journal of Chemistry, Volume 52, page 3996 (1974) by S. Wolfe et al.; the Journal of the American Chemical Society, Volume 96, page 7582 (1974) by B. G. Christensen et al.; and Japanese Patent Application (unexamined publication) no. 49-133,594 claiming priorities based on U.S. Patent Application Nos. 303,905 and 395,662.

However, the above references did not disclose the Compounds I specifically. Now, the present inventors have found the superior antibacterial activity of specific Compounds I and this discovery has led to this invention.

PROBLEMS SOLVED

The said Compounds I are novel antibacterials showing the following characteristics when compared with other types of known 1-oxadethiacephalosporins and commercial cephalosporins:

(1) more potent antibacterial activity against gram-negative bacteria;
(2) higher stability of β-lactam ring;
(3) less dependence of antibacterial activity on the extent of bacterial β-lactamase production;
(4) less dependency on inoculum size;
(5) higher effectiveness against bacteria resistant to certain other cephalosporins (e.g. Enterobacter, Serratia, and indole-positive Proteus);
(6) higher contribution of bactericidal character;
(7) higher blood level;
(8) higher stability in blood; and
(9) lower binding with serum proteins.

SCOPE OF COMPOUNDS

In said formula (I), Ar is 2-thienyl, 3-thienyl, phenyl, p-hydroxyphenyl, p-protected hydroxyphenyl or p-acyloxyphenyl.

In the last mentioned p-acyloxyphenyl, the acyl moiety is an inorganic or organic acyl containing up to 20 carbon atoms (especially 1-5 C alkanoyl, 8-10 C aralkanoyl, 7-10 C aroyl, 2-5 C alkoxycarbonyl, 8-20 C aralkoxycarbonyl, carbamoyl, 2-6 C N-alkylcarbamoyl or ureidocarbonyl).

Specific examples of the acyl group for Ar include formyl, acetyl, propionyl, butyryl, isobutyryl, valeryl, isovaleryl, phenylacetyl, phenylpropionyl, benzoyl, toluoyl, carbomethoxycarbonyl, carbethoxycarbonyl, t-butoxycarbonyl, benzyloxycarbonyl, carbamoyl, N-methylcarbamoyl, N-ethylcarbamoyl, N-propylcarbamoyl, N-isobutylcarbamoyl, N,N-dimethylcarbamoyl, carbamoylcarbamoyl, N$^\alpha$-methylureidocarbonyl and the like acyls.

The protective part in said hydroxy protected p-hydroxyphenyl for Ar is a conventional one for protecting phenolic hydroxy such as esters or ethers. The protective part contains up to 20 carbon atoms. This part is removed to give free hydroxy at a stage of synthesis of Compounds I and the structures of the phenol-protective groups can vary widely without changing the gist of this invention. The structures have no specific significance other than protection, deprotection and, when included, salt formation.

Specific examples of the phenolic hydroxy-protective group include those forming esters including 1-6 C α-haloalkanoyl (e.g. trifluoroacetyl, trichloroacetyl, monochloroacetyl), 1-5 C alkanoyl (e.g. formyl, acetyl, propionyl, butyryl, isopentenoyl), 4-8 C β-ketocarboxylic acyl (e.g. acetoacetyl, 2-12 C alkoxycarbonyl (e.g. t-butoxycarbonyl, cyclopropylmethoxycarbonyl, norbornyloxycarbonyl, 2,2,2-trichloroethoxycarbonyl), 8-15 C aralkoxycarbonyl (e.g. benzyloxycarbonyl, p-methoxybenzyloxycarbonyl, p-nitrobenzyloxycarbonyl, dimethylbenzyloxycarbonyl, diphenylmethoxycarbonyl) and the like acyls for ester groups; and ethers including 1-6 C alkyl (e.g. methyl, isopropyl, t-butyl, t-amyl, cyclopropylmethyl, isobornyl, tetrahydropyranyl, tetrahydrofuranyl, methoxymethyl, ethoxymethyl, methanesulfonyloxymethyl), 7-15 C aralkyl (e.g. benzyl, p-methoxybenzyl, p-methylbenzyl, m-methylbenzyl, p-nitrobenzyl, diphenylmethyl, trityl), 3-8 C trialkylsilyl (e.g. trimethylsilyl, triethylsilyl, dimethyl-t-butylsilyl, methoxydimethylsilyl) and the like groups for ethers.

COB¹ and COB² groups can be carboxy or protected carboxy conventional in the chemistry of penicillins and cephalosporins, usually containing up to 20 carbon atoms. The protected carboxys can be the same or different for each COB¹ and COB² in the same molecule. Usually, the protective groups are removed to give free carboxy or carboxylic salts at a stage of synthesis of Compounds I. Hence, the structures of the carboxy-protective groups can vary widely without changing the gist of this invention. In other words, their structures have no specific significance other than protection, deprotection and, when included, salt formation.

Specific examples of said protected carboxy for COB¹ and COB² are those forming esters (including optionally substituted 1-5 C alkyl esters e.g. methyl, ethyl, isopropyl, n-butyl, t-butyl, pentyl, isopenyl, t-pentyl, cyclopropylmethyl, cyclopropylethyl, monohydroxy-t-butyl, 2,2,2-trichloroethyl, chloromethyl, cyanomethyl, methanesulfonylethyl, acetylmethyl, acetoxymethyl, propionyloxymethyl, pivaloyloxymethyl, benzoyloxymethyl, toluoyloxyethyl, methoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl and allyl esters; aralkyl esters e.g. benzyl, phenethyl, tolylmethyl, dimethylbenzyl, nitrobenzyl, halobenzyl, methoxybenzyl, phthalidyl, p-hydroxydi-t-butylbenzyl, diphenylmethyl, trityl, phenacyl, chlorophenacyl, bromophenacyl, nitrophenacyl, and methylphenacyl esters; and other easily removable aliphatic esters; metal esters e.g. trimethyl silyl, dimethylmethoxysilyl, triethylsilyl, trimethylstannyl esters; and aromatic esters e.g. phenyl, naphthyl, tolyl, dimethylphenyl, nitrophenyl, methanesulfonylphenyl, chlorophenyl, pentachlorophenyl, indanyl and pyridyl esters); hydrazides, amides, or salts including pharmaceutically acceptable salts as given below or salts suitable for reaction or purification.

Pharmaceutically acceptable salts at the carboxylic acid group of Compounds I include alkali metal salts e.g. sodium and potassium salts; alkaline earth metal salts e.g. magnesium, calcium and alkanoyloxycalcium salts; and salts with organic bases e.g. procain and xylocain acting as analgesics.

Some salts are useful during synthesis. Triethylamine, N-methylmorpholine, dimethylaniline or the like base salt can be used as starting material for some reaction, and dicyclohexylamine salt can be used as a well crystallizing compound for purification.

Some carboxy-protective groups are useful for changing the pharmaceutical character of some of carboxylic acids of Compounds I as drugs. In such cases, they can be specifically known groups for drugs conventional in the preparations of β-lactam antibiotics. These groups include those forming the following pharmaceutically acceptable esters e.g. for enhancing the absorption through digestive organs; e.g. phthalidyl, acetoxymethyl, acetoxyethyl, propionyloxyethyl, pivaloyloxymethyl, indanyl, phenyl, tolyl, dimethylphenyl, methoxyphenyl, methoxycarbonyloxyethyl, ethoxycarbonyloxymethyl, phenacyl and like esters.

R group is hydrogen or lower alkyl. Preferable lower alkyls for R are 1–3 C alkyl i.e. methyl, ethyl, propyl and isopropyl.

USE OF COMPOUNDS

Compounds I are strong antibacterials against a variety of gram-positive and gram-negative bacteria, and are useful human medicines, veterinary drugs and disinfectants.

Pharmaceutically acceptable salts of Compounds I given above are suitable for parenteral administration.

Compounds I having p-acyloxyphenyl as Ar are easily hydrolyzed in the presence of serum to show the same order of antibacterial activity with the parent p-hydroxyphenyl compounds.

Compounds I having well-protected carboxy for COB$^1$ and COB$^2$ are useful for preparing deprotected anti-bacterial compounds within or beyond the scope of Compounds I.

Pharmaceutically acceptable esters in Compounds I are usually suitable for enteral administration.

ANTIBACTERIAL ACTIVITY

Compounds I are valuable antibacterials against various gram-positive and gram-negative bacteria, and useful as drugs for human and veterinary use.

They can be used for treating or preventing infections caused by gram-positive bacteria (e.g. *Staphylococcus aureus, Streptococcus pyogenes, Bacillus subtilis, Bacillus cereus, Diplococcus penumoniae, Corynebacterium diphtheriae*) and gram-negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens* at low concentration and some are active even against *Pseudomonas aeruginosa* and anaerobic bacteria (e.g. *Bacteroid fragilis*) at moderate concentration).

Table I shows the antibacterial activity of Compounds I against gram-positive and gram-negative bacteria when minimal inhibitory concentration at inoculum size of $10^6$ is selected as the criterion of the activity.

MEDICAL OR VETERINARY TREATMENT

This invention provides further a method for treating or preventing human or veterinary bacterial infections by administering to the human or animal subject an effective amount of Compound I at a daily dose of e.g. 0.05 to 50 mg/kg body weight for injection or e.g. 0.5 to 100 mg/kg body weight for oral administration, or 1 μg to 1 mg for topical application, at an interval of e.g. 3 to 12 hours, utilizing said superior antibacterial activity.

TABLE I

Minimal Inhibitory Concentrations of Compounds I as sodium salt against some strains of gram-positive and gram-negative bacteria (μg/ml) by the agar-dilution method at pH 7.0

SAMPLES:

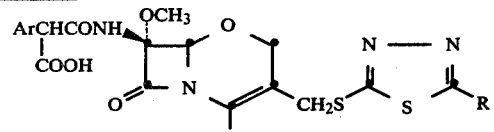

| Compound (1): | Ar = p-hydroxyphenyl and R = methyl; |
| Compound (2): | Ar = p-hydroxyphenyl and R = hydrogen; |
| Compound (3): | Ar = 3-thienyl and R = methyl; and |
| Compound (4): | Ar = 3-thienyl and R = hydrogen. |

BACTERIA:

Gram-positive: *Staphylococcus aureus, Streptococcus pyogenes, Streptococcus pneumoniae*.
Gram-negative: *Escherichia coli, Klepsiella pneumoniae, Proteus mirabilis, Proteus morganii, Proteus vulgaris, Enterobacter cloacae, Serratia marcescens, Pseudomonas aeruminosa*.

| Bacteria | Compound | | | |
|---|---|---|---|---|
| | (1) | (2) | (3) | (4) |
| S. aureus 209P JC-1 | 12.5 | 12.5 | 6.25 | 6.25 |
| S. aureus Smith | 25 | 12.5 | 6.25 | 6.25 |
| S. aureus 077 | 25 | 25 | 6.25 | 6.25 |
| S. aureus C-14 | 25 | 25 | 6.25 | 6.25 |
| S. pyogenes C-203 | 3.13 | 3.13 | 0.78 | 3.13 |
| S. pneumoniae I | 3.13 | 6.25 | 3.13 | 6.25 |
| E. coli H | 0.2 | 0.2 | 0.05 | 0.1 |
| E. coli NIHJ JC-2 | 0.78 | 0.39 | 0.39 | 0.2 |
| E. coli EC-14 | 0.78 | 0.39 | 0.2 | 0.1 |
| E. coli 377 | 1.56 | 0.78 | 0.78 | 0.39 |
| E. coli 73 | 6.25 | 3.13 | 1.56 | 0.78 |
| K. pneumoniae SHIONOGI | 0.78 | 0.39 | 0.2 | 0.2 |
| K. pneumoniae 363 | 0.39 | 0.39 | 0.78 | 0.2 |
| P. mirabilis PR-4 | 0.39 | 0.39 | 0.1 | 0.2 |
| P. morganii No. 9 | 0.78 | 0.78 | 0.2 | 0.2 |
| P. vulgaris CN-329 | 0.39 | 0.78 | 0.1 | 0.2 |
| P. vulgaris No. 3 | 0.78 | 0.78 | 0.39 | 0.39 |
| E. cloacae 233 | 1.6 | 6.25 | 12.5 | 6.25 |
| E. cloacae 13047 | 50 | 25 | 25 | 12.5 |
| S. marcescens 13880 | 3.13 | 1.56 | 1.56 | 0.39 |
| P. aeruginosa 25619 | 25 | 25 | 25 | 25 |

The method is applicable for treating or preventing some diseases caused by bacteria sensitive to Compounds I e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemis, gastroenteritis, enteritis, urinary tract infections, and pyelonephritis, when caused by bacteria sensitive to Compound I.

MEDICAL OR VETERINARY FORMULATIONS:

An effective amount e.g. 0.05 to 100 mg/kg per day of Compound I is given to a subject preferably in a form of enteral or parenteral pharmaceutical or veterinary formulation e.g. solid formulation or liquid formulation by mixing with conventional pharmaceutical or veterinary excipients. The preparations may be in a unit dosage form e.g. tablets, troches, capsules, injections, vials, granules or powder in a unit dosage container or package.

Pharmaceutical or veterinary compositions provided by this invention can be a mixture of 0.01 to 99% of Compound I with a pharmaceutical carrier which can be a solid material or liquid material in which a Compound I is dissolved, dispersed or suspended. The solid compositions can take the form of tablets, powder, dry syrups, troches, granules, capsules, pills, suppositories or like solid preparations. The liquid compositions can take the form of injections, ointments, dispersions, inhalant, suspensions, solutions, emulsions, syrups or elixirs. The formulation can be flavored or colored, and tablets, granules and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricants (e.g. stearic acid, talc, paraffin, boric acid, silica, sodium benzoate, polyethylene glycol, cacao oil, magnesium stearate); emulsifying agents (e.g. lecithin, sorbitan monooleate, acacia); suspending agents (e.g. sorbitol, methyl cellulose, glucose, sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, statilizing agents, analgesics, dispersing agents, wetting agents, antioxidants, and the like excipients can be used, if they do not exert adverse effect on the Compounds, according to methods conventional in the art.

As members of β-lactam antibiotics, Compounds I are not sufficiently stable enough to mix with various substances for a long time. Practically pure compound with some inert additives are the preferable composition for drug (e.g. vials, injections) for commercial distribution in a definite period. Other compositions can be conveniently prepared just before use and used prior to decomposition taking place.

Compounds I having one or more carboxylate salt groups with alkali metal or alkaline earth metal are soluble in water, and conveniently used as solution for intravenous intramuscular or subcutaneous injection or drip according to a conventional method. The compounds can be dissolved in aqueous or oily solvents for injection to give a solution in an ampoule, but generally, more prolonged storage times are possible by making a vial preparation containing crystals, powder, microcrystals or lyophilizate of Compounds I, and dissolving or suspending the drug before use with the said solvents for injection. The preparation may contain preferably said preservative or analgesic. The vial preparation or injection can be given to a patient at a daily dose of e.g. 0.05 to 50 mg/kg body weight depending on the sensitivity of infected bacteria, condition of the patient and interval of administration.

Compounds I, especially those having $COB^1$ and $COB^2$ as a pharmaceutically acceptable ester grouping (e.g. indanyl, acetoxymethyl, pivaloyloxymethyl, ethoxycarbonyloxyethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension, and like oral preparations. These may be the pure compound or a composition comprising Compounds I and said pharmaceutical carrier. The preparation can be made according to the methods conventional in the art, and can be administered to a patient at a daily dose of e.g. 0.5 to 100 mg/kg body weight depending on the condition of patient and sensitivity of infected bacteria.

Further, Compounds I can be used as suppositories, ointments for topical or ocular use, powders for topical use, or like preparations preparable according to methods well known to those skilled in the art. The preparation can contain 0.01 to 99% of Compound I together with a necessary amount of pharmaceutical carrier given above. A necessary amount e.g. 1 μg to 1 mg of the preparation can be applied to the infected part.

The best mode of these methods is to give Compound I to a patient by way of intravenous injection or of drip as aqueous solution for injection.

DISINFECTIONS

Said methods for medical and veterinary use of Compounds I are included in a broader scope of disinfection. This comprises methods for combating bacteria, which comprises administering to the environment an effective amount of Compound I including salt or ester e.g. in a form of conventional formulation, for example, (1) a method for inhibiting the growth of bacteria in an environment;
(2) a method for the prevention or cure of disease in a human or animal;
(3) a method for the prevention of decay in a perishable substance or material; and
(4) a method for disinfecting a substance, material, article or building structure.

By these methods, the bacteria in environment is killed and the environment is disinfected to be kept in desirable condition.

PREFERABLE COMPOUNDS

Compounds I for said methods belong to free acids, carboxylate salts, or esters for pharmaceutical or veterinary use, or for synthesis of the said medical or veterinary useful antibacterial compounds within or beyond the scope of Compounds I.

More preferable Compounds I of this invention include the following ones:

(1) Compound I wherein Ar is p-hydroxyphenyl or 3-thienyl; R is hydrogen or methyl; and $COB^1$ and $COB^2$ each is as defined on page 2, including 7α-methoxy-7β-(α-p-hydroxyphenyl-α-carboxyacetamido)-3-(1,3,4-thiadiazol-5-yl)thiomethyl-1-dethia-1-oxa-3-cephem-4-carboxylic acid and its sodium or potassium salt;

7α-methoxy-7β-(α-p-hydroxyphenyl-α-carboxyacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-[α-(3-thienyl)-α-carboxyacetamido]-3-(1,3,4-thiadiazol-5-yl)thiomethyl-1-dethia-1-oxa-3-cephem-4-carboxylic acid and its sodium or potassium salt; and 7α-methoxy-7β-[α-(3-thienyl)-α-carboxyacetamido]-3-(2-methyl-1,3,4-thiadiazol-5-yl)thiomethyl-1-dethia-1-oxa-3-cephem-4-carboxylic acid and its sodium or potassium salt.

(2) Compound I wherein Ar is p-1-5C alkanoyloxyphenyl; R is hydrogen or methyl; and COB[1] and COB[2] each is as defined on page 2, including 7α-methoxy-7β-(α-p-acetoxyphenyl-α-carboxyacetamido)-3-(1,3,4-thiadiazol-5-yl)thiomethyl-1-dethia-1-oxa-3-cephem-4-carboxylic acid and its sodium or potassium salt;

7α-methoxy-7β-(α-p-acetoxyphenyl-α-carboxyacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-(α-p-propionyloxyphenyl-α-carboxyacetamido)-3-(1,3,4-thiadiazol-5-yl)thiomethyl-1-dethia-1-oxa-3-cephem-4-carboxylic acid and its sodium or potassium salt;

7α-methoxy-7β-(α-p-propionyloxyphenyl-α-carboxyacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-(α-p-butyryloxyphenyl-α-carboxyacetamido)-3-(1,3,4-thiadiazol-5-yl)thiomethyl-1-dethia-1-oxa-3-cephem-4-carboxylic acid and its sodium or potassium salt; and 7α-methoxy-7β-(α-p-butyryloxyphenyl-α-carboxyacetamido)-3-(2-methyl-1,3,4-thiadiazol-5-yl)thiomethyl-1-dethia-1-oxa-3-cephem-4-carboxylic acid and its sodium or potassium salt.

(3) Compound I wherein Ar is p-hydroxyphenyl or 3-thienyl; R is hydrogen, methyl or propyl; COB[1] is a pharmaceutically acceptable carboxylate ester group; and COB[2] is carboxy, protected carboxy or a carboxylate salt group, including 7α-methoxy-7β-[α-p-hydroxyphenyl-α-(5-indanyl)-oxycarbonylacetamido]-3-(1,3,4-thiadiazol-5-yl)thiomethyl-1-dethia-1-oxa-3-cephem-4-carboxylic acid and its sodium or potassium salt;

7α-methoxy-7β-[α-p-hydroxyphenyl-α-(5-indanyl)oxycarbonylacetamido]-3-(2-methyl-1,3,4-thiadiazol-5-yl)thiomethyl-1-dethia-1-oxa-3-cephem-4-carboxylic acid and its sodium or potassium salt;

7α-methoxy-7β-(α-p-hydroxyphenyl-α-pivaloyloxymethoxycarbonylacetamido)-3-(1,3,4-thiadiazol-5-yl)thiomethyl-1-dethia-1-oxa-3-cephem-4-carboxylic acid and its sodium or potassium salt;

7-α-methoxy-7β-(α-p-hydroxyphenyl-α-acetoxymethoxycarbonylacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-(α-p-hydroxyphenyl-α-phenoxycarbonylacetamido)-3-(1,3,4-thiadiazol-5-yl)thiomethyl-1-dethia-1-oxa-3-cephem-4-carboxylic acid and its sodium or potassium salt;

7α-methoxy-7β-(α-p-hydroxyphenyl-α-phenoxycarbonylacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-(α-p-hydroxyphenyl-α-tolyloxycarbonylacetamido)-3-(1,3,4-thiadiazol-5-yl)thiomethyl-1-dethia-1-oxa-3-cephem-4-carboxylic acid and its sodium or potassium salt; and 7α-methoxy-7β-[α-(3-thienyl)-α-phenoxycarbonylacetamido]-3-(2-ethyl-1,3,4-thiadiazol-5-yl)thiomethyl-1-dethia-1-oxa-3-cephem-4-carboxylic acid and its sodium or potassium salt;

(4) Other antibacterially preferable Compounds I including:

7α-methoxy-7β-(α-phenyl-α-carboxyacetamido)-3-(1,3,4-thiadiazol-5-yl)thiomethyl-1-dethia-1-oxa-3-cephem-4-carboxylic acid and its sodium or potassium salt;

7α-methoxy-7β-(α-phenyl-α-carboxyacetamido)-3-(2-methyl-1,3,4-thiadiazol-5-yl)thiomethyl-1-dethia-1-oxa-3-cephem-4-carboxylic acid and its sodium or potassium salt;

7α-methoxy-7β-[α-(2-thienyl)-α-carboxyacetamido]-3-(1,3,4-thiadiazol-5-yl)thiomethyl-1-dethia-1-oxa-3-cephem-4-carboxylic acid and its sodium or potassium salt; and 7α-methoxy-7β-[α-(2-thienyl)-α-carboxyacetamido]-3-(2-propyl-1,3,4-thiadiazol-5-yl)thiomethyl-1-dethia-1-oxa-3-cephem-4-carboxylic acid and its sodium or potassium salt.

(5) Preferable Compounds I useful mainly as intermediates in which Ar is p-benzyloxyphenyl, p-dimethylbenzyloxyphenyl, p-methoxybenzyloxyphenyl, p-nitrobenzyloxyphenyl, p-tetrahydropyranyloxyphenyl or p-3 to 8C-trialkylsilyloxyphenyl; R is hydrogen or methyl; and COB[1] and COB[2] each is as defined on page 2, including 7α-methoxy-7β-(α-p-benzyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester.

7α-methoxy-7β-(α-benzyloxyphenyl-α-carboxyacetamido)-3-(2-methyl-1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-methoxybenzyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-methoxybenzyloxyphenyl-α-carboxyacetamido)-3-(2-methyl-1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-butoxycarbonyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-butoxycarbonyloxyphenyl-α-carboxyacetamido)-3-(2-methyl-1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-tetrahydropyranyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-tetrahydropyranyloxyphenyl-α-carboxyacetamido)-3-(2-methyl-1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-trimethylsilyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-triethylsilyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester;

7-α-methoxy-7β-(α-p-triethylsilyloxyphenyl-α-carboxyacetamido)-3-(2-methyl-1,3,4-thiadiazol-5-yl)thiomethyl-1-dethia-1-oxa-3-cephem-4-carboxylic acid and its benzyl, p-methoxybenzyl or diphenylmethyl ester;

7α-methoxy-7β-(α-p-t-butyldimethylsilyloxyphenyl-α-carboxyacetamido)-3-(1,3,4-thiadiazol-5-yl)thiomethyl-1-dethia-1-oxa-3-cephem-4-carboxylic acid and its benzyl, p-methoxybenzyl or diphenylmethyl ester; and 7α-methoxy-7β-(α-p-t-butyldimethylsilyloxyphenyl-α-carboxyacetamido)-3-(2-methyl-1,3,4-thiadiazol-5-yl)-thiomethyl-1-dethia-1-oxa-3-cephem-4-carboxylic acid and its benzyl, p-methoxybenzyl or diphenylmethyl ester.

SYNTHESIS

(1) ACYLATION

Reaction of Amine (II) or its reactive derivative with Arylmalonic acid (III) or its reactive derivative gives Compound I.

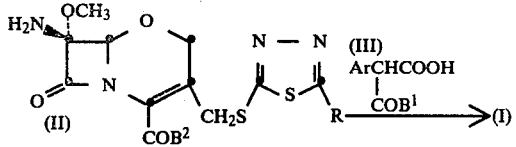

(wherein Ar, COB¹, COB² and R are as defined above)

Amine II has been prepared according to a method described in Japanese Unexamined Patent Publication No. 49-133,594. The reactive derivatives thereof include those 7-amino of which is pretreated in a conventional manner to give silyl (e.g. trimethylsilyl, methoxydimethylsilyl), stannyl (e.g. trimethylstannyl), carbonyl, alkenyl (e.g. enamino formation with acetone, acetylacetone, acetoacetate, acetoacetonitrile, acetoacetamide, acetoacetanilide, cyclopentanedione, acetylbutyrolactone) or alkylidene (e.g. 1-haloalkylidene, 1-haloaralkylidene, 1-alkoxy-1-phenoxyalkylidene) derivative group or to give an acid addition salt group (e.g. mineral acid, carboxylic acid, sulfonic acid salts).

Arylmalonic acid III may be prepared from known compounds in a conventional manner e.g. Japanese Unexamined Patent Publication No. 51-1489; German Patent Application OLS 2,451,931; Journal of the American Chemical Society, 59, 1901 (1937); Journal of Medicinal Chemistry, 18, 172 (1975). COB¹ can be one of said protected carboxy. The reactive derivatives of Arylmalonic acid III include acid anhydrides, acid halides, reactive esters, reactive amides, azides, and the like functional derivatives.

This reaction can be carried out as follows:

(i) Free acid III—Amine II or its reactive derivative is reacted in a conventional manner with free acid III in the presence of a condensing reagent such as carbodiimide (e.g. N,N'-diethylcarbodiimide, N,N'-dicyclohexylcarbodiimide), carbonyl compounds (e.g. carbonyldiimidazole), isoxazolinium salts, acylamino compounds (e.g. 2-ethoxy-1-ethoxycarbonyl-1,2-dihydroquinoline), amidase or like reagent usually and preferably in an aprotic solvent (e.g. halohydrocarbons, nitriles, ethers, amides and mixtures thereof). Preferable molar ratio of reactants is 1 to 2 free acid III and 1 to 2 condensing reagent against Amine II.

(ii) Acid anhydrides of III—Amine II or its reactive derivative is reacted in a conventional manner with an acid anhydride of Arylmalonic acid III. Such anhydrides include those with alkoxyformic acid, aralkoxyformic acid, sulfuric acid, sulfurous acid, phosphoric acid, phosphorous acid, aliphatic or aromatic carboxylic acid or sulfonic acid, such special intramolecular anhydrides as ketene or nitrile oxide, symmetrical anhydride and like reactive anhydrides. This reaction can be carried out in the presence of an acid acceptor such as inorganic base (e.g. oxide, hydroxide, carbonate, bicarbonate, or like of alkali metal or alkaline earth metal), organic base (e.g. tertiary amine, aromatic amine), oxirane (e.g. alkyleneoxide, aralkyleneoxide), amides (e.g. N,N-dimethylformamide, N,N-dimethylacetamide, hexamethylphosphorotriamide), adsorbent (e.g. Molecular sieves), and like acid acceptor, preferably in an aprotic solvent (e.g. halohydrocarbon, nitrile, ether, ketone, amide, ester or their mixture). Preferable molar ratio is 1 to 2 acid anhydride and 1 to 10 acid acceptor against Amine II or reactive derivative thereof.

(iii) Acid halide of III—Amine II or its reactive derivative is reacted with an acid halide or azide in the presence of an acid acceptor as mentioned above in an aprotic solvent (e.g. halohydrocarbon, nitrile, ether, ketone, water, dialkylamide or their mixture). Preferable molar ratio is 1 to 2 acid halide and 1 to 10 acid acceptor against Amine II or its reactive derivative.

(iv) Reactive esters and Reactive amides—According to conventional manner, Amine II is reacted with a reactive ester such as enolic ester (e.g. vinyl ester, isopropenyl ester), aryl ester (e.g. halophenyl ester, nitrophenyl ester) heteroaromatic ester (e.g. ester with 1-hydroxybenzotriazole), ester with hydroxylamine, ester with oxim or diacylhydroxylamine, or like reactive ester; or a reactive amide such as aromatic amides (e.g. amides with imidazole, triazole, or 2-ethoxy-1,2-dihydroquinoline), diacylanilide or like conventional reactive amide; or other reactive derivative (including formimino compounds e.g. N,N-dimethylformimino ester) in an aprotic solvent as referred to above. Preferable molar ratio of the reactants are 1 to 10 reactive derivative of III against Amine II or its derivative at −15° to 80° C., usually at around room temperature.

(2) THIADIAZOLYLTHIO GROUP INTRODUCTION

Reaction of 7β-arylmalonamido-7α-methoxy-3-substituted methyl-1-oxadethia-3-cephem-4-carboxylic acid or its derivative (IV) with 1,3,4-thiadiazol-5-ylthiol (V) or its derivative.

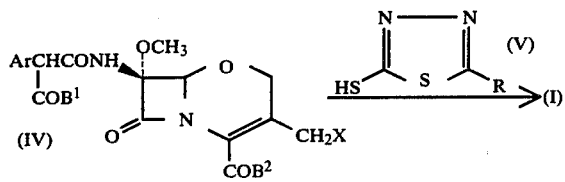

(wherein Ar, COB¹, COB² and R are as defined above; and

X is a functional reactive group replaceable with compound V at the thiol group)

Representative X groups are halogen or acyloxy such as phosphoryloxy, sulfonyloxy, dihaloacetoxy, and trihaloacetoxy.

The reactive derivatives of Compound V include alkali metal salts, organic base salts (e.g. triethylamine salt) and like derivatives.

The reactive of above scheme is carried out in the presence of a base, preferably in a solvent (e.g. halohydrocarbon, ether, ketone, or amide solvent).

In a special case, X can be hydroxy which is added to ring double bond to form epoxy, that is to say Compound IV is 7β-arylmalonamido-7α-methoxy-3-epoxymethano-1-oxadethia-3-cephem-4-carboxylic acid derivative.

(3) METHOXYLATION

Introduction of 7α-methoxy group to 7α-hydrogen compound, 7β-arylmalonamido-3-(1,3,4-thiadiazol-5-yl)thiomethyl-1-oxadethia-3-cephem-4-carboxylic acid or its derivative according to the following reaction scheme:

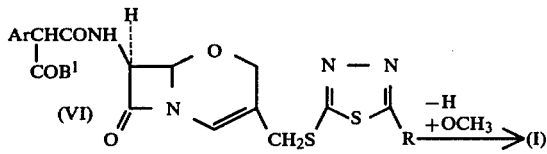

(wherein Ar, COB¹, COB² and R are as defined above)

This reaction is carried out by:

(a) treatment of Compound VI with an N-halogenating reagent (e.g. t-butyl hypochlorite) and alkali metal methoxide (e.g. sodium methoxide, potassium methoxide), in methanol and then reduction of over-halogenated by-products;

(b) treatment of Compound VI with an N-halogenating reagent in the presence of phenyllithium or sodium borate, and then with base in methanol; and (c) other methods including that using halogen and 1,5-diazabicycloundecene (DBU) as the N-halogenating reagent.

All of these methods go through acylimino intermediates, to which methanol adds giving objective Compound I.

(4) DEPROTECTION AT CARBOXY

Deprotection of the protected carboxy for COB¹ and COB² to give Compound I having free carboxy:

(i) in the cases of highly reactive esters, amides, and anhydrides, the deprotection can be achieved by hydrolysis with aqueous acid, base or buffer, (ii) Haloethyl, benzyl, nitrobenzyl, methylbenzyl, dimethylbenzyl, diarylmethyl and triarylmethyl esters can be cleaved into the corresponding free acid under mild reductive condition (e.g. acid and tin, zinc, chromous salt, or the like) or by catalytic hydrogenation in the presence of a catalyst (e.g. platinum, palladium, nickel) or sodium dithionite reduction, (iii) Benzyl, methoxybenzyl, methylbenzyl, dimethoxybenzyl, t-alkyl, trityl, diarylmethyl, cyclopropylmethyl, sulfonylethyl and cyclopropylmethyl esters can be removed by solvolytic reaction to free acid on treatment with an acid (e.g. mineral acid, Lewis acid, sulfonic acid, strongly acidic carboxylic acid), if required, in the presence of a cation acceptor e.g. anisole, and (iv) Phenacyl, ethinyl and p-hydroxy-3,5-di-t-butylbenzyl esters may be cleaved into free acid on treatment with a base or other nucleophilic reagent. Highly reactive phenacyl esters can be removed with irradiation of light to give carboxylic acid.

(5) Deprotection at Phenolic Group of Ar

Representative deprotections are as follows:

(i) esters and ethers (particularly benzyl ethers and α-oxygenated ethers) as referred to above can be deprotected by treating with an acid (e.g. mineral acid, Lewis acid, strongly acidic carboxylic acid, sulfonic acid, other acids given above, if required in the presence of a cation acceptor such as anisole. Hydrolytic condition can also be applied.

(ii) Benzyloxyformic ester or benzyl ethers can be deprotected by catalytic hydrogenation using a catalyst such as platinum, palladium or nickel.

This reaction (5) sometimes takes place simultaneously with said reaction (4). Such cases are included in the scope of this invention.

(6) Formation of Salts or Ester of Compounds I

By conventional methods, Compound I having free carboxy or phenolic group forms salts on treatment with an organic or inorganic base usually by mixing both reactants. Conventional esterification of Compound I having free carboxy or phenolic group forms an ester as given before.

All of these reactions (1) to (6) can be carried out at a temperature of about −30° C. to 100° C., preferably at −20° C. to 50° C. The solvent may optionally be selected from halohydrocarbons (e.g. dichloromethane, chloroform, dichloroethane, trichloroethane, chlorobenzene), ethers (e.g. diethyl ether, tetrahydrofuran, tetrahydropyrane, anisole), ketones (e.g. acetone, methyl ethyl ketone, methyl isobutyl ketone, cyclohexanone, acetophenone), esters (e.g. ethyl acetate, butyl acetate, methyl benzoate), nitrohydrocarbons (e.g. nitromethane), nitriles (e.g. acetonitrile, benzonitrile), amides (e.g. formamide, acetamide, dimethylformamide, dimethylacetamide, hexamethylphosphorotriamide), sulfoxides, acids (e.g. formic acid, acetic acid), bases (e.g. butylamine, triethylamine, pyridine, picoline, quinoline), alcohols (e.g. methanol, ethanol, pentanol, benzylalcohol), water and like conventional solvents when suitable. They may be used as a mixture of two or more of said solvents.

The reaction can be accelerated, if required, by stirring while excluding moisture under an inert gas.

The objective products can be isolated from the reaction mixture by removing the used solvent, unchanged reactants, by-products and other contaminants by e.g. conventional concentration, extraction, adsorption, elution, washing, chromatography, recrystallization, and the like methods.

EXAMPLES

Following Examples illustrate the compounds and process of this invention. They are not intended to restrict the scope of the invention. Abbreviations are those well established in the art.

EXAMPLE 1

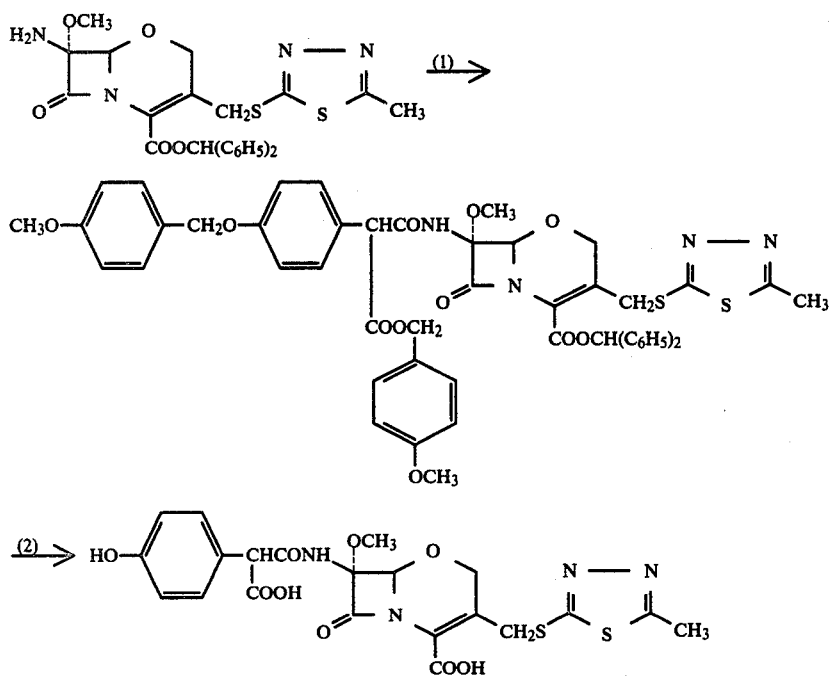

(1) A suspension of 375 mg of α-(4-p-methoxybenzyloxyphenyl)-α-p-methoxybenzyloxycarbonylacetic acid in 5 ml of methylene chloride is stirred at −15° C. under nitrogen atmosphere. Triethylamine (90 µl) and oxalyl chloride (55 µl) are added thereto and the reaction mixture is stirred for 1 hour under ice-cooling, mixed with a solution of 228 mg of diphenylmethyl 7α-methoxy-7β-amino-3-(2-methyl-1,3,4-thiadiazol-5-yl)thiomethyl-1-dethia-1-oxa-3-cephem-4-carboxylate in 5 ml of methylene chloride containing 52 µl of pyridine, stirred for 30 minutes under ice-cooling, and concentrated under reduced pressure. The residue is dissolved in ethyl acetate, washed with 2N-hydrochloric acid, water, 5% aqueous sodium hydrogencarbonate and then water, dried and concentrated. The residue is purified by chromatography on a column of 20 g of silica gel to yield 212 mg of diphenylmethyl 7α-methoxy-7β-[α-(4-p-methoxybenzyloxyphenyl)-α-p-methoxybenzyloxycarbonylacetamido]-3-(2-methyl-1,3,4-thiadiazol-5-yl)thiomethyl-1-dethia-1-oxa-3-cephem-4-carboxylate in 52% yield.

IR: $\nu_{max}^{CHCl_3}$ 3405, 3320, 1783, 1717, 1605, 1583 cm$^{-1}$.

NMR: $\delta_{DSS}^{CDCl_3}$ 2.64s3H, 3.44s3H/2, 3.46s3H/2, 3.79s6H, 4.18ABq(13 Hz)1H, 4.52ABq(13 Hz)1H, 4.52brs2H, 4.58s1H, 4.96s2H, 5.02s1H, 5.12s2H.

(2) To a solution of 212 mg of the product prepared in the above (1) in 2 ml of methylene chloride are added 1 ml of anisole and 0.5 ml of trifluoroacetic acid at 0° C. under nitrogen atmosphere while stirring, and the mixture stirred at 0° C. for 30 minutes and concentrated under reduced pressure. The residue is washed with ether to yield 110 mg of 7α-methoxy-7β-(α-p-hydroxyphenyl-α-crboxyacetamido)-3-(2-methyl-1,3,4-thiadiazol-5-yl)thiomethyl-1-dethia-1-oxa-3-cephem-4-carboxylic acid in 94% yield. mp. 118° C. (decomposition).

IR: $\nu_{max}^{KBr}$ 3380, 2570, 1781, 1719, 1613, 1514 cm$^{-1}$.

UV: $\lambda_{max}^{CH_3OH}$ 227 mµ (ε=14160), 275.5 mµ (ε=11800). $[\alpha]_D$ −40.0±1.5° (c=0.547, CH$_3$OH).

NMR: $\delta_{DSS}^{D_2O-NaHCO_3}$ 2.68s3H, 3.44s3H/2, 3.50s3H/2, 3.92ABq(14 Hz)1H, 4.42ABq(14 Hz)1H, 4.45brs2H, 5.08s1H, 6.83A$_2$B$_2$(8 Hz)2H, 7.25A$_2$B$_2$(8 Hz)2H.

EXAMPLE 2

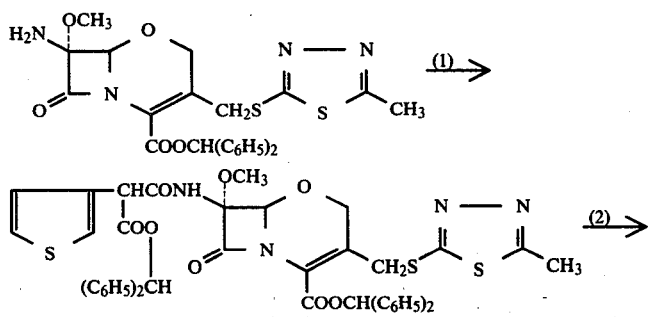

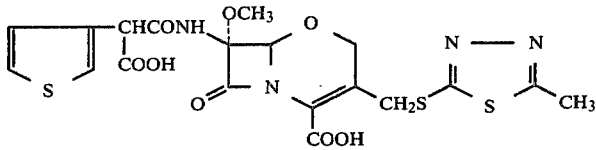

(1) To a suspension of 268 mg of α-(3-thienyl)-α-diphenylmethoxycarbonylacetic acid in 4 ml of methylene chloride are added 79 μl of triethylamine and 49 μl of oxalyl chloride under ice-cooling, and the mixture is stirred for 20 minutes, mixed with a solution of 200 mg of diphenylmethyl 7α-methoxy-7β-amino-3-(2-methyl-1,3,4-thiadiazol-5-yl)thiomethyl-1-dethia-1-oxa-3-cephem-4-carboxylate in 4 ml of methylene chloride containing 46 μl of pyridine and stirred for 15 minutes under ice-cooling. The reaction mixture is diluted with ethyl acetate, washed with 2 N hydrochloric acid, water, 5% aqueous sodium hydrogencarbonate and water, dried, and concentrated under reduced pressure. The residue is purified by chromatography on silica gel containing 10% water to yield 302 mg of diphenylmethyl 7α-methoxy-7β-[α-(3-thienyl)-α-diphenylmethoxycarbonylacetamido]-3-(2-methyl-1,3,4-thiadiazol-5-yl)thiomethyl-1-dethia-1-oxa-3-cephem-4-carboxylate in 93% yield.

IR: $\nu_{max}^{CHCl_3}$ 3400, 3330, 1782, 1720, 1700, 1625, 1600 cm$^{-1}$.

NMR: $\delta_{DSS}^{CDCl_3}$ 2.62s3H, 3.36s3H, 4.12ABq(14 Hz)1H, 4.48ABq(14 Hz)1H, 4.42s2H, 4.83s1H, 4.96s1H, 6.89s1H.

(2) To a solution of 302 mg of the product prepared in the above (1) in 4 ml of methylene chloride are added 0.5 ml of anisole and 0.4 ml of trichloroacetic acid at 0° C. under nitrogen atmosphere, and the mixture is stirred at the same temperature for 30 minutes and concentrated under reduced pressure. The residue is washed with ether to yield 180 mg of 7α-methoxy-7β-[α-(3-thienyl)-α-carboxyacetamido]-3-(2-methyl-1,3,4-thiadiazol-5-yl)thiomethyl-1-dethia-1-oxa-3-cephem-4-carboxylic acid in 97% yield. mp. >105° C. (decomposition)

IR: $\nu_{max}^{KBr}$ 3270, 2550, 1784, 1714, 1634 cm$^{-1}$.

UV: $\lambda_{max}^{CH_3OH}$ 274 mμ (ε=11050) $[\alpha]_D^{26}$ −36.6°±1.5° (c=0.524, CH$_3$OH).

NMR: $\delta_{DSS}^{D_2O+NaHCO_3}$ 2.73s3H, 3.46s3H/2. 3.53s3H/2, 3.95ABq(13 Hz)1H, 4.47ABq(13 Hz)1H, 4:50brs2H, 5.12s1H.

EXAMPLE 3

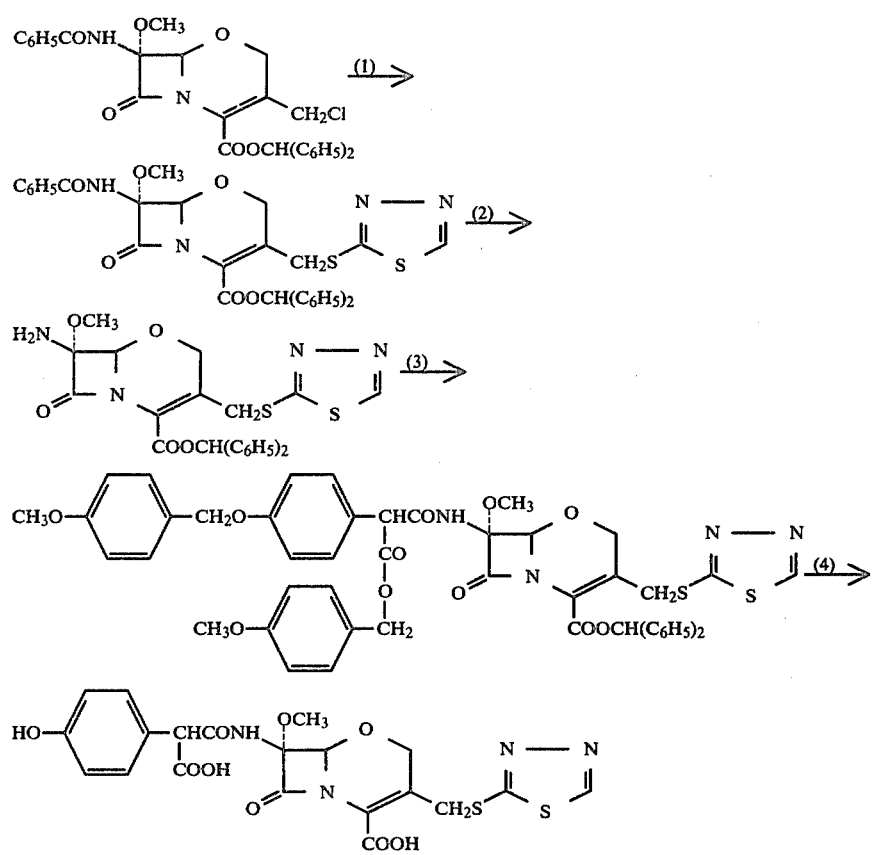

(1) To a solution of 400 mg of 1,3,4-thiadiazol-2-thiol in 6 ml of methanol is added 6 ml of 0.565 M sodium methoxide/methanol, and the mixture stirred for 20 minutes and concentrated. The residue is dissolved in 5 ml of dimethylformamide, poured into a solution of 1.50 g of diphenylmethyl 7β-benzamido-7α-methoxy-3-chloromethyl-1-dethia-1-oxa-3-cephem-4-carboxylate under ice-cooling, stirred at the same temperature for 20 minutes, poured into water and extracted with ethyl acetate. The extract is washed with water, dried, and concentrated under reduced pressure. The residue is chromatographed on a column of 50 g of silica gel containing 10% water and eluted with a mixture of benzene and ethyl acetate (2:1). The eluate is concentrated to yield 1.25 g of diphenylmethyl 7β-benzamido-7α-methoxy-3-(1,3,4-thiadiazol-2-yl)thiomethyl-1-dethia-1-oxa-3-cephem-4-carboxylate in 72.6% yield.

NMR: $\delta_{DSS}{}^{CDCl_3}$ 3.62s3H, 4.23ABq(14 Hz)1H+4.52ABq(14 Hz)1H, 4.58s2H, 5.17s1H, 6.93s1H, 8.88s1H.

(2) To a solution of 1.25 g of the product prepared above in 3 ml of methylene chloride are added 327 μl of pyridine and 762 mg of phosphorus pentachloride at 0° C. under nitrogen atmosphere while stirring, and the mixture stirred at room temperture for 2 hours, cooled to −30° C., mixed with 14 ml of methanol, stirred at 0° C. for 90 minutes and at room temperature for 30 minutes, and cooled with ice again. The reaction mixture is mixed with 1.9 ml of diethylamine, stirred for 10 minutes, and concentrated to about half volume under reduced pressure. The residue is poured into water and extracted with ethyl acetate. The extract is washed with water, dried and concentrated under reduced pressure. The residue is chromatographed on a column of silica gel containing 10% water and eluted with a mixture of benzene and ethyl acetate to yield 676 mg of diphenylmethyl 7β-amino-7α-methoxy-3-(1,3,4-thiadiazol-5-yl)thiomethyl-1-dethia-1-oxa-3-cephem-4-carboxylate in 65% yield.

NMR: $\delta_{DSS}{}^{CDCl_3}$ 2.22brs2H, 3.50s3H, 4.25ABq(14 Hz)1H+4.57ABq(14 Hz)1H, 4.67s2H, 4.87s1H, 6.93s1H, 8.93s1H.

(3) To a suspension of 262 mg of α-p-methoxybenzyloxycarbonyl-α-(4-p-methoxybenzyloxyphenyl)acetic acid in 3 ml of methylene chloride are added 62 μl of triethylamine and 39 μl of oxalyl chloride at −15° C., and the mixture stirred for 1 hour under ice-cooling to yield the corresponding acid halide.

To a solution of 150 mg of the product prepared in the above (2) in 2 ml of methylene chloride are added 36 μl of pyridine and the acid halide prepared above, and the mixture stirred for 20 minutes, mixed with 2 ml of water, and concentrated under reduced pressure. The residue is extracted with ethyl acetate. The extract is washed with 2 N hydrochloric acid, water, 5% aqueous sodium hydrogencarbonate and then water, dried and concentrated under reduced pressure. The residue is chromatographed on a column of 10 g of silica gel containing 10% water and eluted with a mixture of benzene and ethyl acetate (4:1) to yield 153 mg of diphenylmethyl 7β-[α-p-methoxybenzyloxycarbonyl-α-(4-p-methoxybenzyloxyphenyl)acetamido]-7α-methoxy-3-(1,3,4-thiadiazol-2-yl)thiomethyl-1-dethia-1-oxa-3-cephem-4-carboxylate in 55% yield.

NMR: $\delta_{DSS}{}^{CDCl_3}$ 3.43s3H, 3.73s3H, 3.77s3H, 4.50s2H, 4.60s1H, 4.22ABq(14 Hz)1H, 4.53ABq(14 Hz)1H, 4.93s2H, 5.00s1H, 5.12s2H, 8.87s1H.

IR: $\nu_{max}{}^{CHCl_3}$ 1790, 1722, 1700, 1612 cm$^{-1}$.

(4) To a solution of 150 mg of the product prepared in the above (3) in 2 ml of methylene chloride are added 0.7 ml of anisole and 0.5 ml of trifluoroacetic acid under ice-cooling, and the mixture is stirred for 25 minutes and concentrated under reduced pressure. The residue is washed with ether to yield 78 mg of 7α-methoxy-7β-(α-p-hydroxyphenyl-α-carboxyacetamido)-3-(1,3,4-thiadiazol-5-yl)thiomethyl-1-dethia-1-oxa-3-cephem-4-carboxylic acid in 92% yield. mp. >120° C. (decomposition)

IR: $\nu_{max}{}^{Nujol}$ 3260, 3180, 1785, 1720, 1612 cm$^{-1}$.

NMR: $\delta_{DSS}{}^{D_2O+NaHCO_3}$ 3.47s3H/2, 3.53s3H/2, 4.02ABq(14 Hz)1H, 4.23ABq(14 Hz)1H, 4.50brs3H, 6.87A$_2$B$_2$q(8 Hz)2H, 7.29A$_2$B$_2$q(8 Hz)2H, 9.42s1H. $[\alpha]_D{}^{25}$ −34.0°±1.5° (c=0.5036, CH$_3$OH).

EXAMPLE 4

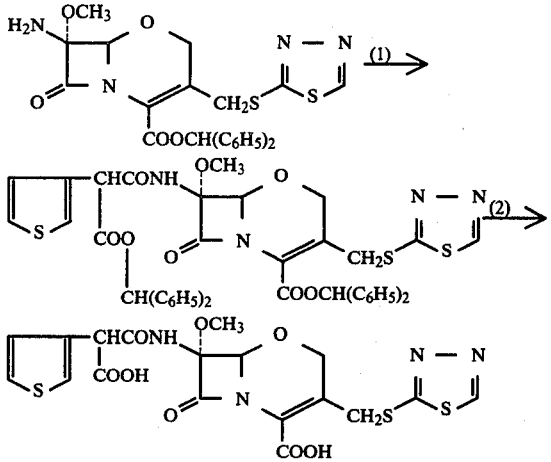

(1) To a solution of 212 mg of α-diphenylmethoxycarbonyl-α-(3-thienyl)acetic acid in 3 ml of methylene chloride are added 79 μl of triethylamine and 49 μl of oxalyl chloride under ice-cooling, and the mixture stirred for 20 minutes to yield the corresponding acid halide.

To a solution of 150 mg of diphenylmethyl 7β-amino-7α-methoxy-3-(1,3,4-thiadiazol-2-yl)thiomethyl-1-dethia-1-oxa-3-cephem-4-carboxylate in 2 ml of methylene chloride are added 36 μl of pyridine and the acid halide prepared above under ice-cooling while stirring, and the mixture stirred for 20 minutes, extracted with ethyl acetate, washed with 2 N hydrochloric acid, water, 5% aqueous sodium hydrogencarbonate and water, dried and concentrated under reduced pressure. The residue is purified by chromatography on a column of 10 g of silica gel containing 10% water to yield 235 mg of diphenylmethyl 7α-methoxy-7β-[α-(3-thienyl)-α-diphenylmethoxycarbonylacetamido]-3-(1,3,4-thiadiazol-2-yl)thiomethyl-1-dethia-1-oxa-3-cephem-4-carboxylate in 93% yield.

IR: $\nu_{max}{}^{CHCl_3}$ 3390, 3310, 1785, 1720, 1700 cm$^{-1}$.

NMR: $\delta_{DSS}{}^{CDCl_3}$ 3.42s2H, 4.20ABq(14 Hz)1H, 4.47brs2H, 4.55ABq(14 Hz)1H, 4.87s1H, 5.00s1H, 6.92s2H, 8.92s1H.

(2) To a solution of 235 mg of the product prepared in the above (1) in 1.5 ml of methylene chloride are added 1 ml of anisole and 0.5 ml of trifluoroacetic acid at 0° C. under stirring, and the mixture stirred at the same temperature for 1 hour and concentrated under reduced pressure. The residue is washed with ether to yield 140 mg of 7α-methoxy-7β-[α-carboxy-α-(3-thienyl)acetamido]-3-(1,3,4-thiadiazol-2-yl)thiomethyl-1-dethia-1-oxa-3-cephem-4-carboxylic acid in 98% yield. mp. >110° C.

IR: $\nu_{max}{}^{Nujol}$ 3275, 1785, 1710 cm$^{-1}$.

NMR: $\delta_{DSS}{}^{DSS+D_2O}$ 3.47s3H/2, 3.52s3H/2, 4.00d(14 Hz)1H, 4.32d(14 Hz)1H, 4.50brs3H, 5.10s1H, 9.43s1H.

(IR and NMR are measured in a form of sodium salt which is prepared on reaction with sodium 2-ethylhexanoate.)

EXAMPLE 5

A sterile solution of 7β-(α-p-hydroxyphenyl-α-carboxyacetamido)-7α-methoxy-3-(1,3,4-thiadiazol-2-yl)thiomethyl-1-dethia-1-oxa-3-cephem-4-carboxylic acid disodium salt (0.1 g) in distilled water for injection (1 ml) is injected intravenously at 6 hour interval to a patient suffering from urinary tract infection caused by *Escherichia coli.*

EXAMPLE 6

A sterile solution of 7β-[α-(3-thienyl)-α-carboxyacetamido]-7α-methoxy-3-(1,3,4-thiadiazol-2-yl)thiomethyl-1-dethia-1-oxa-3-cephem-4-carboxylic acid disodium salt (0.5 g) in physiological saline (100 ml) is dripped intravenously to a patient suffering from pneumonitis caused by *Klebsiella pneumoniae.*

EXAMPLE 7

A solution of sterile neutral lyophilizate of 7β-(α-p-hydroxyphenyl-α-carboxyacetamido)-7α-methoxy-3-(2-methyl-1,3,4-thiadiazol-5-yl)thiomethyl-1-dethia-1-oxa-3-cephem-4-carboxylic acid (0.2 g) in physiological saline (2 ml) is injected to pre-operative human subject for preventing infection during or after the operation.

EXAMPLE 8

A gelatine capsule containing 7β-[α-(3-thienyl)-α-indanyloxycarbonylacetamido]-7α-methoxy-3-(2-methyl-1,3,4-thiadiazol-5-yl)thiomethyl-1-dethia-1-oxa-3-cephem-4-carboxylic acid (0.2 g), corn starch (0.05 g) and magnesium stearate (0.05 g) is given orally three times a day to a patient suffering from septicemia.

What we claim is:

1. A compound of the formula:

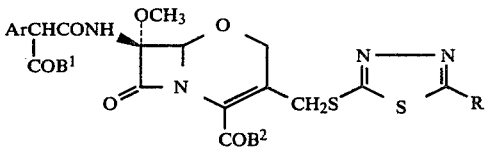

wherein

Ar is phenyl, p-hydroxyphenyl, p-1–5C alkanoyloxyphenyl, p-benzyloxyphenyl, p-dimethylbenzyloxyphenyl, p-methoxybenzyloxyphenyl, p-nitrobenzyloxyphenyl, p-tetrahydropyranyloxyphenyl, p-3–8C trialkylsilyloxyphenyl, 3-thienyl or 2-thienyl;

R is hydrogen or 1–3C alkyl; and

COB¹ and COB² each is carboxy, protected carboxy or a carboxylate salt group.

2. A compound as claimed in claim 1, wherein Ar is p-hydroxyphenyl or 3-thienyl.

3. A compound as claimed in claim 1, wherein R is hydrogen or methyl.

4. A compound as claimed in claim 1, wherein
Ar is p-hydroxyphenyl or 3-thienyl;
R is hydrogen or methyl; and
COB¹ and COB² each is carboxy, protected carboxy or a carboxylate salt group.

5. The compound as claimed in claim 4, that is 7α-methoxy-7β-(α-p-hydroxyphenyl-α-carboxyacetamido)-3-(1,3,4-thiadiazol-5-yl)thiomethyl-1-dethia-1-oxa-3-cephem-4-carboxylic acid.

6. The compound as claimed in claim 4, that is 7α-methoxy-7β-(α-p-hydroxyphenyl-α-carboxyacetamido)-3-(1,3,4-thiadiazol-5-yl)thiomethyl-1-dethia-1-oxa-3-cephem-4-carboxylic acid sodium salt.

7. The compound as claimed in claim 4, that is 7α-methoxy-7β-(α-p-hydroxyphenyl-α-carboxyacetamido)-3-(1,3,4-thiadiazol-5-yl)thiomethyl-1-dethia-1-oxa-3-cephem-4-carboxylic acid potassium salt.

8. The compound as claimed in claim 4, that is 7α-methoxy-7β-(α-p-hydroxyphenyl-α-carboxyacetamido)-3-(2-methyl-1,3,4-thiadiazol-5-yl)thiomethyl-1-dethia-1-oxa-3-cephem-4-carboxylic acid.

9. The compound as claimed in claim 4, that is 7α-methoxy-7β-(α-p-hydroxyphenyl-α-carboxyacetamido)-3-(2-methyl-1,3,4-thiadiazol-5-yl)thiomethyl-1-dethia-1-oxa-3-cephem-4-carboxylic acid sodium salt.

10. The compound as claimed in claim 4, that is 7α-methoxy-7β-(α-p-hydroxyphenyl-α-carboxyacetamido)-3-(2-methyl-1,3,4-thiadiazol-5-yl)thiomethyl-1-dethia-1-oxa-3-cephem-4-carboxylic acid potassium salt.

11. The compound as claimed in claim 4, that is 7α-methoxy-7β-[α-(3-thienyl)-α-carboxyacetamido]-3-(1,3,4-thiadiazol-5-yl)thiomethyl-1-dethia-1-oxa-3-cephem-4-carboxylic acid.

12. The compound as claimed in claim 4, that is 7α-methoxy-7β-[α-(3-thienyl)-α-carboxyacetamido]-3-(1,3,4-thiadiazol-5-yl)thiomethyl-1-dethia-1-oxa-3-cephem-4-carboxylic acid sodium salt.

13. The compound as claimed in claim 4, that is 7α-methoxy-7β-[α-(3-thienyl)-α-carboxyacetamido]-3-(1,3,4-thiadiazol-5-yl)thiomethyl-1-dethia-1-oxa-3-cephem-4-carboxylic acid potassium salt.

14. The compound as claimed in claim 4, that is 7α-methoxy-7β-[α-(3-thienyl)-α-carboxyacetamido]-3-(2-methyl-1,3,4-thiadiazol-5-yl)thiomethyl-1-dethia-1-oxa-3-cephem-4-carboxylic acid.

15. The compound as claimed in claim 4, that is 7α-methoxy-7β-[α-(3-thienyl)-α-carboxyacetamido]-3-(2-methyl-1,3,4-thiadiazol-5-yl)thiomethyl-1-dethia-1-oxa-3-cephem-4-carboxylic acid sodium salt.

16. The compound as claimed in claim 4, that is 7α-methoxy-7β-[α-(3-thienyl)-α-carboxyacetamido]-3-(2-methyl-1,3,4-thiadiazol-5-yl)thiomethyl-1-dethia-1-oxa-3-cephem-4-carboxylic acid potassium salt.

17. A compound as claimed in claim 1, wherein
Ar is p-1 to 5C alkanoyloxyphenyl;
R is hydrogen or methyl; and
COB¹ and COB² each is carboxy, protected carboxy or a carboxylate salt group.

18. A compound as claimed in claim 17, that is 7α-methoxy-7β-(α-p-acetoxyphenyl-α-carboxyacetamido)-3-(1,3,4-thiadiazol-5-yl)thiomethyl-1-dethia-1-oxa-3-cephem-4-carboxylic acid or its sodium or potassium salt.

19. A compound as claimed in claim 17, that is 7α-methoxy-7β-(α-p-acetoxyphenyl-α-carboxyacetamido)-3-(2-methyl-1,3,4-thiadiazol-5-yl)thiomethyl-1-dethia-1-oxa-3-cephem-4-carboxylic acid or its sodium or potassium salt.

20. A compound as claimed in claim 17, that is 7α-methoxy-7β-(α-p-propionyloxyphenyl-α-carboxyacetamido)-3-(1,3,4-thiadiazol-5-yl)thiomethyl-1-dethia-1-oxa-3-cephem-4-carboxylic acid or its sodium or potassium salt.

21. A compound as claimed in claim 17, that is 7α-methoxy-7β-(α-p-propionyloxyphenyl-α-carboxyacetamido)-3-(2-methyl-1,3,4-thiadiazol-5-yl)thiomethyl-1-dethia-1-oxa-3-cephem-4-carboxylic acid or its sodium or potassium salt.

22. A compound as claimed in claim 17, that is 7α-methoxy-7β-(α-p-butyryloxyphenyl-α-carboxyacetamido)-3-(1,3,4-thiadiazol-5-yl)thiomethyl-1-dethia-1-oxa-3-cephem-4-carboxylic acid or its sodium or potassium salt.

23. A compound as claimed in claim 17, that is 7α-methoxy-7β-(α-p-butyryloxyphenyl-α-carboxyacetamido)-3-(2-methyl-1,3,4-thiadiazol-5-yl)thiomethyl-1-dethia-1-oxa-3-cephem-4-carboxylic acid or its sodium or potassium salt.

24. A compound as claimed in claim 1, wherein
Ar is p-hydroxyphenyl or 3-thienyl;
R is hydrogen, methyl or propyl;
$COB^1$ is a pharmaceutically acceptable carboxylate ester group; and
$COB^2$ is carboxy, protected carboxy or a carboxylate salt group.

25. A compound as claimed in claim 24, that is 7α-methoxy-7β-[α-p-hydroxyphenyl-α-(5-indanyl)oxycarbonylacetamido]-3-(1,3,4-thiadiazol-5-yl)thiomethyl-1-dethia-1-oxa-3-cephem-4-carboxylic acid or its sodium or potassium salt.

26. A compound as claimed in claim 24, that is 7α-methoxy-7β-[α-p-hydroxyphenyl-α-(5-indanyl)oxycarbonylacetamido]-3-(2-methyl-1,3,4-thiadiazol-5-yl)thiomethyl-1-dethia-1-oxa-3-cephem-4-carboxylic acid or its sodium or potassium salt.

27. A compound as claimed in claim 24, that is 7α-methoxy-7β-(α-p-hydroxyphenyl-α-pivaloyloxymethoxycarbonylacetamido)-3-(1,3,4-thiadiazol-5-yl)thiomethyl-1-dethia-1-oxa-3-cephem-4-carboxylic acid or its sodium or potassium salt.

28. A compound as claimed in claim 24, that is 7α-methoxy-7β-(α-p-hydroxyphenyl-α-acetoxymethoxycarbonylacetamido)-3-(2-methyl-1,3,4-thiadiazol-5-yl)thiomethyl-1-dethia-1-oxa-3-cephem-4-carboxylic acid or its sodium or potassium salt.

29. A compound as claimed in claim 24, that is 7α-methoxy-7β-(α-p-hydroxyphenyl-α-phenoxycarbonylacetamido)-3-(1,3,4-thiadiazol-5-yl)thiomethyl-1-dethia-1-oxa-3-cephem-4-carboxylic acid or its sodium or potassium salt.

30. A compound as claimed in claim 24, that is 7α-methoxy-7β-(α-p-hydroxyphenyl-α-phenoxycarbonylacetamido)-3-(2-methyl-1,3,4-thiadiazol-5-yl)thiomethyl-1-dethia-1-oxa-3-cephem-4-carboxylic acid or its sodium or potassium salt.

31. A compound as claimed in claim 24, that is 7α-methoxy-7β-(α-p-hydroxyphenyl-α-tolyloxycarbonylacetamido)-3-(1,3,4-thiadiazol-5-yl)thiomethyl-1-dethia-1-oxa-3-cephem-4-carboxylic acid or its sodium or potassium salt.

32. A compound as claimed in claim 24, that is 7α-methoxy-7β-[α-(3-thienyl)-α-phenoxycarbonylacetamido]-3-(2-ethyl-1,3,4-thiadiazol-5-yl)thiomethyl-1-dethia-1-oxa-3-cephem-4-carboxylic acid or its sodium or potassium salt.

33. A compound as claimed in claim 1, that is 7α-methoxy-7β-(α-phenyl-α-carboxyacetamido)-3-(1,3,4-thiadiazol-5-yl)thiomethyl-1-dethia-1-oxa-3-cephem-4-carboxylic acid or its sodium or potassium salt.

34. A compound as claimed in claim 1, that is 7α-methoxy-7β-(α-phenyl-α-carboxyacetamido)-3-(2-methyl-1,3,4-thiadiazol-5-yl)thiomethyl-1-dethia-1-oxa-3-cephem-4-carboxylic acid or its sodium or potassium salt.

35. A compound as claimed in claim 1, that is 7α-methoxy-7β-[α-(2-thienyl)-α-carboxyacetamido]-3-(1,3,4-thiadiazol-5-yl)thiomethyl-1-dethia-1-oxa-3-cephem-4-carboxylic acid or its sodium or potassium salt.

36. A compound as claimed in claim 1, that is 7α-methoxy-7β-[α-(2-thienyl)-α-carboxyacetamido]-3-(2-propyl-1,3,4-thiadiazol-5-yl)thiomethyl-1-dethia-1-oxa-3-cephem-4-carboxylic acid or its sodium or potassium salt.

37. A compound as claimed in claim 1, wherein
Ar is p-benzyloxyphenyl, p-dimethylbenzyloxyphenyl, p-methoxybenzyloxyphenyl, p-nitrobenzyloxyphenyl, p-tetrahydropyranyloxyphenyl or p-3 to 8C-trialkylsilyloxyphenyl;
R is hydrogen or methyl; and
$COB^1$ and $COB^2$ each is carboxy, protected carboxy or a carboxylate salt group.

38. A compound as claimed in claim 37, that is 7α-methoxy-7β-(α-benzyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

39. A compound as claimed in claim 37, that is 7α-methoxy-7β-(α-benzyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

40. A compound as claimed in claim 37, that is 7α-methoxy-7β-(α-p-methoxybenzyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

41. A compound as claimed in claim 37, that is 7α-methoxy-7β-(α-p-methoxybenzyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

42. A compound as claimed in claim 37, that is 7α-methoxy-7β-(α-p-butoxycarbonyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

43. A compound as claimed in claim 37, that is 7α-methoxy-7β-(α-p-butoxycarbonyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

44. A compound as claimed in claim 37, that is 7α-methoxy-7β-(α-p-tetrahydropyranyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

45. A compound as claimed in claim 37, that is 7α-methoxy-7β-(α-p-tetrahydropyranyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

46. A compound as claimed in claim 37, that is 7α-methoxy-7β-(α-p-trimethylsilyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

47. A compound as claimed in claim 37, that is 7α-methoxy-7β-(α-p-triethylsilyloxyphenyl-α-carboxyacetamido)-3-(1,3,4-thiadiazol-5-yl)thiomethyl-1- dethia-1-oxa-3-cephem-4-carboxylic acid or its benzyl, p-methoxybenzyl or diphenylmethyl ester.

48. A compound as claimed in claim 37, that is 7α-methoxy-7β-(α-p-triethylsilyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

49. A compound as claimed in claim 37, that is 7α-methoxy-7β-(α-p-t-butyldimethylsilyloxyphenyl-α-carboxyacetamido)-3-(1,3,4-thiadiazol-5-yl)thiomethyl-1-dethia-1-oxa-3-cephem-4-carboxylic acid or its benzyl, p-methoxybenzyl or diphenylmethyl ester.

50. A compound as claimed in claim 37, that is 7α-methoxy-7β-(α-p-t-butyldimethylsilyloxyphenyl-α-carboxyacetamido)-3-(2-methyl-1,3,4-thiadiazol-5-yl)thiomethyl-1-dethia-1-oxa-3-cephem-4-carboxylic acid or its benzyl, p-methoxybenzyl or diphenylmethyl ester.

51. A pharmaceutical or veterinary formulation which comprises a bactericidally effective amount of a compound as claimed in claim 1 together with a pharmaceutically acceptable or veterinarily acceptable, respectively, diluent, carrier or excipient.

52. A pharmaceutical or veterinary composition consisting of 0.01 to 99% of a compound according to claim 1 and a pharmaceutically or veterinarily acceptable carrier.

53. A pharmaceutical or veterinary composition as claimed in claim 51 in the form of an injectable composition in an ampoule or vial.

54. A pharmaceutical or veterinary composition as claimed in claim 53 in the form of sterilized microcrystals or lyophilizate.

55. A composition as claimed in claim 51 in unit dosage form.

56. A pharmaceutical or veterinary composition as claimed in claim 51, wherein the compound is that having p-hydroxyphenyl, p-1 to 5C alkanoyloxyphenyl, 2-thienyl or 3-thienyl as Ar; hydrogen or methyl as R; carboxy, a pharmaceutical or veterinarily acceptable carboxylate salt group or pharmaceutically or veterinarily acceptable ester group as $COB^1$; and carboxy or a pharmaceutically or veterinarily acceptable salt group as $COB^2$.

57. A pharmaceutical or veterinary composition as claimed in claim 51, wherein the compound has p-hydroxyphenyl or 3-thienyl as Ar; carboxy or sodium or potassium carboxylate salt groups as $COB^1$ and $COB^2$ and hydrogen or methyl as R.

58. A method for the prevention or cure of a bacterial disease in a human or animal subject, which comprises administering to the subject a bactericidally effective amount of a compound as claimed in claim 1.

59. A method as claimed in clam 58, wherein the disease is bacterial infectious disease selected from pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections and pyelonephritis when caused by bacteria sensitive to the compound.

60. A method as claimed in claim 58, wherein the compound is administered at a daily dose of 0.05 to 50 mg per kilogram body weight for injection; 0.05 to 100 mg per body weight for oral administration; or 1 μg to 1 mg for topical application.

61. A method as claimed in claim 58 when effected by intravenous injection or drip.

62. A method as claimed in claim 58, wherein the compound has p-hydroxyphenyl or 3-thienyl as Ar; carboxys or sodium or potassium carboxylate salt groups as $COB^1$ and $COB^2$; and hydrogen or methyl as R.

* * * * *